US009512052B2

(12) United States Patent
Long et al.

(10) Patent No.: US 9,512,052 B2
(45) Date of Patent: Dec. 6, 2016

(54) ADSORPTION DESULFURIZATION PROCESS FOR HYDROCARBONS AND A REACTION APPARATUS THEREFOR

(71) Applicants: CHINA PETROLEUM & CHEMICAL CORPORATION, Beijing (CN); RESEARCH INSTITUTE OF PETROLEUM PROCESSING, SINOPEC, Beijing (CN)

(72) Inventors: Jun Long, Beijing (CN); Zhihong Tian, Beijing (CN); Shuandi Hou, Beijing (CN); Bingtian Zhu, Beijing (CN); Xuefeng Wu, Beijing (CN); Jiushun Zhang, Beijing (CN); Anguo Mao, Beijing (CN); Zhemin Zhang, Beijing (CN); Lufeng Lv, Beijing (CN); Jinlong He, Beijing (CN); Xuefeng Li, Beijing (CN); Yalin Liu, Beijing (CN)

(73) Assignees: CHINA PETROLEUM & CHEMICAL CORPORATION, Beijing (CN); RESEARCH INSTITUTE OF PETROLEUM PROCESSING, SINOPEC, Beijing (CN)

( * ) Notice: Subject to any disclaimer, the term of this patent is extended or adjusted under 35 U.S.C. 154(b) by 181 days.

(21) Appl. No.: 14/065,582

(22) Filed: Oct. 29, 2013

(65) Prior Publication Data

US 2014/0121438 A1 May 1, 2014

(30) Foreign Application Priority Data

Oct. 29, 2012 (CN) .......................... 2012 1 0419823
Oct. 29, 2012 (CN) .......................... 2012 1 0420999

(51) Int. Cl.
*B01J 8/24* (2006.01)
*B01J 8/26* (2006.01)
(Continued)

(52) U.S. Cl.
CPC ................ *C07C 7/12* (2013.01); *B01J 8/0055* (2013.01); *B01J 8/24* (2013.01); *B01J 8/26* (2013.01);
(Continued)

(58) Field of Classification Search
CPC ......... B01J 8/0055; C10G 25/09; C10G 45/20
See application file for complete search history.

(56) References Cited

U.S. PATENT DOCUMENTS

| 2,784,803 A | * | 3/1957 | Saxton | ................... B01J 8/0055 208/161 |
| 4,486,207 A | * | 12/1984 | Baillie | ................... B01D 45/12 209/718 |

(Continued)

FOREIGN PATENT DOCUMENTS

| CN | 1158281 A | 9/1997 |
| EA | 010716 B1 | 10/2008 |

(Continued)

*Primary Examiner* — Jennifer A Leung
(74) *Attorney, Agent, or Firm* — Novick, Kim & Lee, PLLC; Allen Xue

(57) ABSTRACT

The present invention relates to an airflow particle sorter, comprising: a top-sealed sorter main body, a discharge port, an outtake tube and at least one directing-intake port; the inner space of the sorter main body, from the above to the bottom, includes, a straight tube zone and a cone zone, the conical bottom of the cone zone is connected to the straight tube zone; the discharge port is located at the bottom of the cone zone; the directing-intake port is installed in the upper part of the straight tube zone in a tangential direction of the straight tube zone, and is communicated with the inner space of the sorter main body; the outtake tube is hermetically (Continued)

inserted into the top of the sorter main body, and extends downwardly to the lower part of the straight tube zone, and the outtake tube has a sealed bottom end; the lower part of the outtake tube is installed with at least one directing-outtake port, which communicates the outtake tube with the inner space of the sorter main body, the directing-outtake port is installed in a tangential direction of the outtake tube. The present invention further relates to a fluidized bed reactor and an adsorption desulfurization reaction apparatus as well as an adsorption desulfurization process.

20 Claims, 4 Drawing Sheets

(51) Int. Cl.
| | |
|---|---|
| *C10G 25/09* | (2006.01) |
| *C10G 25/12* | (2006.01) |
| *C10G 45/20* | (2006.01) |
| *C07C 7/12* | (2006.01) |
| *B01J 8/00* | (2006.01) |
| *C10G 45/02* | (2006.01) |

(52) U.S. Cl.
CPC .............. *C10G 25/09* (2013.01); *C10G 25/12* (2013.01); *C10G 45/02* (2013.01); *C10G 45/20* (2013.01)

(56) References Cited

U.S. PATENT DOCUMENTS

| | | | |
|---|---|---|---|
| 5,776,416 A | 7/1998 | Oda | |
| 6,202,854 B1 | 3/2001 | Krieser et al. | |
| 6,679,930 B1* | 1/2004 | An | A47L 9/1608 55/337 |
| 2003/0188993 A1* | 10/2003 | Khare | C10G 25/06 208/208 R |
| 2003/0194356 A1* | 10/2003 | Meier | B01D 53/0407 422/141 |
| 2004/0251168 A1 | 12/2004 | Meier et al. | |
| 2005/0067326 A1 | 3/2005 | Vaughn et al. | |

FOREIGN PATENT DOCUMENTS

| | | | | |
|---|---|---|---|---|
| GB | 754041 A | * | 8/1956 | ............. C10G 35/14 |
| GB | 868043 A | * | 5/1961 | ................ B01J 8/44 |

* cited by examiner

A-A

ADSORPTION DESULFURIZATION PROCESS FOR HYDROCARBONS AND A REACTION APPARATUS THEREFOR

TECHNICAL FIELD

The present invention relates to an airflow particle sorter, an adsorption desulfurization reaction apparatus comprising the airflow particle sorter, and an adsorption desulfurization process using the adsorption desulfurization reaction apparatus.

BACKGROUND ART

In the adsorption desulfurization for hydrocarbons, the sulfur element in the hydrocarbon feedstock is fixed, e.g. by converting the sulfur element in sulfur containing hydrocarbons to zinc sulfide. By passing oxygen to the regenerator and combusting therein, zinc sulfide in the catalyst particles and oxygen are reacted to form zinc oxide and sulfur dioxide, and therefore the adsorption activity of the catalyst is recovered.

Because the sulfur element has a larger atom radius than the oxygen element, therefore in the reaction-regeneration cycle, it is inevitable that the crystal lattice of the catalyst changes and even the crushing of catalyst particles may occur, resulting in the formation of catalyst fine powder. In addition, in the multiphase fluidized bed reactor, the reaction gas and the catalyst are contacted with each other. Under the action of the reaction stream, the catalyst is kept in a fluidized state. After the long term collision and abrasion among catalyst particles, the crushing will occur, which also results in the formation of catalyst fine powder.

The current S-Zorb adsorption desulfurization process uses the fluidized adsorption reactor. The reaction product leaves the reactor through a dust filter located on the top of the reactor, and the solid particles leave the reactor through a discharging tube located below the reaction stream in the upper bed of the reactor and enter the regenerator and then the reducer for regeneration and reduction. In the fluidized absorption reactor, the powder in the catalyst and the powder formed by the long-term abrasion of catalyst particles are raised up to the settling space of the reactor and kept in suspension for long period. The suspended powder and particles have no chance to return to the dense bed of the reactor or to be discharged from the reactor, and therefore will have an effluence on the stable run of the apparatus.

In the existing adsorption desulfurization apparatus for the catalytic gasoline, a built-in metal filter is generally used to recover the catalyst. However, the metal filter has a small pore diameter and mainly recovers the superfine catalyst powder. The solid particles having a size of e.g. greater than 2 μm is prone to remain in the reaction system, resulting in that a large amount of catalyst fine powder with a smaller particle size cannot be duly removed from the reactor, and therefore the desulfurization effect and the normal operation are impacted.

The catalyst for adsorption desulfurization has a lower mechanical strength than other solid catalysts. Where a conventional cyclone separator is provided in the adsorption desulfurization reactor to separate the catalyst, due to the high gas flow rate in the cyclone separator, upon separating the hydrocarbon product from catalyst particles, there will be intense collision among particles and between the particles and the cyclone separator's walls, which is prone to cause the crushing of the catalyst. Moreover, there is a centrifugal force field with high turbulent flow in the cyclone separator. Various size particles have different turbulent flow strengths. This results in that the catalyst fine powder in the fluidized bed reactor cannot be effectively separated and sorted out. Furthermore, due to the substantive crushing of catalyst, the quantity of the catalyst fine powder in the fluidized bed reactor increases, and therefore the catalyst consumes faster. Therefore, in general, the cyclone separator is not chosen as a component for separating and sorting the catalyst in adsorption desulfurization reactor.

Therefore, it is urgent to provide a new adsorption desulfurization reaction apparatus, which can not only accomplish the adsorption desulfurization and the regeneration and reduction of the catalyst, but also can duly remove the fine catalyst powder formed in the system from the reaction system to ensure the desulfurization effect, and accomplish stable and long-term run of the apparatus. Moreover, when separating and sorting the catalyst particles, it is required that no or substantially no secondary crushing of catalyst particles appears. Based on this, it still needs a sorter that can effectively separate solid particles with larger size from a gas stream entraining solid particles, and will not exacerbate the crushing of catalyst particles.

CONTENTS OF INVENTION

Aiming at the prior problems in the adsorption desulfurization, the present invention provides an airflow particle sorter.

According to an embodiment, the airflow particle sorter of the present invention comprises:

a top-sealed sorter main body, a discharge port, an outtake tube and at least one directing-intake port;

the inner space of the sorter main body, from the above to the bottom, includes, a straight tube zone and a cone zone, the conical bottom of the cone zone is connected to the straight tube zone;

the discharge port is located at the bottom of the cone zone;

the directing-intake port is installed in the upper part of the straight tube zone in a tangential direction of the straight tube zone, and is communicated with the inner space of the sorter main body;

the outtake tube is hermetically inserted into the top of the sorter main body, and extends downwardly to the lower part of the straight tube zone, and the outtake tube has a sealed bottom end;

the lower part of the outtake tube is installed with at least one directing-outtake port, which communicates the outtake tube with the inner space of the sorter main body, the directing-outtake port is installed in a tangential direction of the outtake tube.

The airflow particle sorter of the present invention, when separating a gas stream entraining solid particles, can separate out solid particles with larger particle size, and the separated solid particles have low content of the entrained fine powder.

According to the airflow particle sorter of the present invention, the inner space of the sorter main body comprises the straight tube zone and the cone zone, the directing-intake port and the directing-outtake port are located in the straight tube zone and separated by a certain distance with each other, and a sealed bottom end is located under the directing-outtake port. When the airflow particle sorter separates and sorts the solid particles in the gas stream entering the inner space of the sorter main body, the inner space can provide a stable centrifugal force field for the separation and sorting so as to obtain solid particles with larger particle size.

Upon separating a gas stream entraining solid particles by means of the airflow particle sorter of the present invention, the gas stream has a low flow rate and a stable flow in the inner space of the sorter main body, so as to decrease the probability of crushing the solid particles.

Aiming at the prior problems in the adsorption desulfurization, the present invention provides an adsorption desulfurization reaction apparatus.

According to an embodiment, the adsorption desulfurization reaction apparatus of the present invention comprises a fluidized bed reactor, a catalyst regenerator, a catalyst reducer, an optional catalyst fine powder catcher, and an optional fine powder classificator, wherein the fluidized bed reactor comprises a top-sealed reactor main body, at least one airflow particle sorter and at least one stream inlet, the inner space of the reactor main body, from the above to the bottom, includes, a settling zone and a reaction zone, the stream inlet is located at the bottom of the reaction zone;

wherein the airflow particle sorter comprises:

a top-sealed sorter main body, a discharge port, an outtake tube and at least one directing-intake port;

the inner space of the sorter main body, from the above to the bottom, includes, a straight tube zone and a cone zone, the conical bottom of the cone zone is connected to the straight tube zone;

the discharge port is located at the bottom of the cone zone;

the directing-intake port is installed in the upper part of the straight tube zone in a tangential direction of the straight tube zone, and is communicated with the inner space of the sorter main body;

the outtake tube is hermetically inserted into the top of the sorter main body, and extends downwardly to the lower part of the straight tube zone, and the outtake tube has a sealed bottom end;

the lower part of the outtake tube is installed with at least one directing-outtake port, which communicates the outtake tube with the inner space of the sorter main body, the directing-outtake port is installed in a tangential direction of the outtake tube;

the sorter main body of the airflow particle sorter is located in the settling zone, the outtake tube hermetically passes through the top of the fluidized bed reactor, the directing-intake port is communicated with the settling zone, and the discharge port downward extends into the reaction zone.

The adsorption desulfurization reaction apparatus of the present invention can not only accomplish the adsorption desulfurization of a sulfur-containing hydrocarbon feedstock and the regeneration and reduction of a spent catalyst, but also duly remove the fine catalyst powder produced in the adsorption desulfurization from the adsorption desulfurization reactor.

The airflow particle sorter of the adsorption desulfurization reaction apparatus of the present invention can effectively sort out catalyst particles with larger particle size from the hydrocarbon-catalyst mixture coming from the settling zone, and send them back to the reaction zone. The fine catalyst powder is sent out of the fluidized bed reactor together with hydrocarbon products. The reason why the airflow particle sorter can achieve the above effect lies in that: the inner space of the sorter main body comprises the straight tube zone and the cone zone, the directing-intake port and the directing-outtake port are located in the straight tube zone and separated by a certain distance with each other, and a sealed bottom end is located under the directing-outtake port. In the adsorption desulfurization condition, when the airflow particle sorter separates and sorts catalyst particles in the hydrocarbon-catalyst mixture entering the inner space of the sorter main body, the inner space can provide a stable centrifugal force field for the separation and sorting so as to accomplish the sorting of catalyst particles in the hydrocarbon-catalyst mixture and effectively remove the fine catalyst powder from the fluidized bed reactor.

In the separation space of the airflow particle sorter in the adsorption desulfurization reaction apparatus of the present invention, the gas stream has a low flow rate and a stable flow, and therefore there is a low probability for secondarily crushing the catalyst during the separation and sorting.

Aiming at the prior problems in the adsorption desulfurization, the present invention provides an adsorption desulfurization process.

The adsorption desulfurization process of the present invention is conducted in the adsorption desulfurization reaction apparatus provided in the present invention, the process comprises: contacting a sulfur-containing hydrocarbon feedstock and an adsorption desulfurization catalyst in the reaction zone of the fluidized bed reactor to remove at least a portion of sulfur element in the hydrocarbon feedstock; subjecting the obtained hydrocarbon-catalyst mixture successively to separation in the settling zone, the airflow particle sorter, the optional catalyst fine powder catcher, and the optional fine powder classificator to obtain hydrocarbon products and a spent catalyst; introducing at least a part of the spent catalyst to the catalyst regenerator to regenerate it; reducing the regenerated catalyst in the catalyst reducer, and recycling at least a part of the reduced catalyst to the reaction zone.

The adsorption desulfurization process of the present invention, due to the use of the adsorption desulfurization reaction apparatus of the present invention, can duly remove the fine catalyst powder produced in the adsorption desulfurization from the fluidized bed reactor, therefore avoid the accumulation of the fine catalyst powder in the fluidized bed reactor, make the adsorption desulfurization reaction apparatus be able to run stably for a long period, and produce a good and stable desulfurization effect. Furthermore, there is a low probability for secondarily crushing the catalyst during the catalyst particle separation and sorting, and therefore the catalyst consumption and the apparatus operation cost can be reduced.

In summary, the following technical schemes are disclosed:

1. An airflow particle sorter, comprising:

a top-sealed sorter main body, a discharge port, an outtake tube and at least one directing-intake port;

the inner space of the sorter main body, from the above to the bottom, includes, a straight tube zone and a cone zone, the conical bottom of the cone zone is connected to the straight tube zone;

the discharge port is located at the bottom of the cone zone;

the directing-intake port is installed in the upper part of the straight tube zone in a tangential direction of the straight tube zone, and is communicated with the inner space of the sorter main body;

the outtake tube is hermetically inserted into the top of the sorter main body, and extends downwardly to the lower part of the straight tube zone, and the outtake tube has a sealed bottom end;

the lower part of the outtake tube is installed with at least one directing-outtake port, which communicates the outtake tube with the inner space of the sorter main body, the directing-outtake port is installed in a tangential direction of the outtake tube.

2. The airflow particle sorter according to any of previous schemes, wherein the ratio of the length of the portion of the outtake tube inserting into the sorter main body to the length of straight tube zone is 0.6-1, e.g. 0.7-1, 0.8-1, 0.9-1, or 0.95-1.

3. The airflow particle sorter according to any of previous schemes, wherein the cone zone is present in a form of an inverse truncated cone.

4. The airflow particle sorter according to any of previous schemes, wherein the ratio of the height of the straight tube zone to the height of the cone zone can be 0.4-1.5:1, e.g. 0.5-1:1, such as 0.6-0.8:1.

5. The airflow particle sorter according to any of previous schemes, wherein the directing-intake port is installed in a tangential direction of the straight tube zone.

6. The airflow particle sorter according to any of previous schemes, wherein the directing-outtake port is installed in a tangential direction of the outtake tube.

7. The airflow particle sorter according to any of previous schemes, wherein the number of the directing-intake port and the number of the directing-outtake port are respectively at least one.

8. The airflow particle sorter according to any of previous schemes, wherein the number of the directing-intake port and the number of the directing-outtake port can be identical or different, preferably identical.

9. The airflow particle sorter according to any of previous schemes, wherein the distance from the lower edge of the directing-intake port to the bottom of the straight tube zone is H1, the distance from the lower edge of the directing-outtake port to the bottom of the straight tube zone is H2, the ratio of H1/H2 can be 1:0.1-0.8, preferably 1:0.2-0.6.

10. The airflow particle sorter according to any of previous schemes, wherein the directing-intake port is installed in the upper part of the straight tube zone, preferably the upper edge of the directing-intake port is aligned with the top of the straight tube zone;

11. The airflow particle sorter according to any of previous schemes, wherein the directing-outtake port is installed in the lower part of the outtake tube, preferably the lower edge of the directing-outtake port is aligned with the bottom of the outtake tube.

12. The airflow particle sorter according to any of previous schemes, wherein the difference between the horizontal cross-section area of the straight tube zone and the horizontal cross-section area of the outtake tube is A0, the total cross-section area perpendicular to the airflow direction of the directing-intake port is A1, the total cross-section area perpendicular to the airflow direction of the directing-outtake port is A2, A1/A0 is 0.01-0.8:1, preferably 0.02-0.6:1; A2/A0 is 0.01-0.5:1, preferably 0.015-0.4:1.

13. The airflow particle sorter according to any of previous schemes, wherein the ratio of the cross-section area perpendicular to the airflow direction of the outtake tube to the horizontal cross-section area of the straight tube zone is 0.01-0.7:1, preferably 0.04-0.6:1.

14. The airflow particle sorter according to any of previous schemes, wherein when the number of the directing-intake port is more than one, the more than one directing-intake ports are distributed in the circumferential direction of the straight tube zone, preferably equal interval.

15. The airflow particle sorter according to any of previous schemes, wherein when the number of the directing-outtake port is more than one, the more than one directing-outtake ports are distributed in the circumferential direction of the outtake tube, preferably equal interval.

16. A fluidized bed reactor, which comprises a top-sealed reactor main body, at least one airflow particle sorter and at least one stream inlet, wherein the inner space of the reactor main body, from the above to the bottom, includes, a settling zone and a reaction zone, wherein the stream inlet is located at the bottom of the reaction zone, wherein the airflow particle sorter is the airflow particle sorter according to any one of schemes 1-15, wherein the sorter main body of the airflow particle sorter is located in the settling zone, the outtake tube hermetically passes through the top of the fluidized bed reactor, the directing-intake port is communicated with the settling zone, and the discharge port downward extends into the reaction zone.

17. The fluidized bed reactor of scheme 16, wherein the ratio of the total cross-section area perpendicular to the airflow direction of the directing-intake port of the airflow particle sorter to the horizontal cross-section area of the settling zone is 0.01-0.4:1, preferably 0.05-0.3:1.

18. An adsorption desulfurization reaction apparatus, which comprises a fluidized bed reactor, an optional catalyst regenerator, an optional catalyst reducer, an optional catalyst fine powder catcher, and an optional fine powder classificator, wherein the fluidized bed reactor is the fluidized bed reactor of scheme 16 or 17.

19. The adsorption desulfurization reaction apparatus of scheme 18, wherein the adsorption desulfurization reaction apparatus further comprises a catalyst fine powder catcher installed out of the reactor main body, the feed port of the catalyst fine powder catcher is communicated with the outtake tube of the airflow particle sorter.

20. The adsorption desulfurization reaction apparatus of any one of schemes 18-19, wherein the catalyst fine powder catcher includes a discharge tube, wherein the discharge tube hermetically passes through the side wall of the reactor main body, inserts into the reactor main body, and extends into the reaction zone.

21. The adsorption desulfurization reaction apparatus of any one of schemes 18-20, wherein the catalyst fine powder catcher comprises a discharge tube, the discharge tube of the catalyst fine powder catcher is communicated with a feed port of a fine powder classificator, which fine powder classificator comprises a discharge tube for receipt of larger catalyst particles sorted out by the fine powder classificator, the discharge tube hermetically passes through the side wall of the reactor main body, inserts into the reactor main body and extends into the reaction zone.

22. An adsorption desulfurization process, which is conducted in the fluidized bed reactor of any one of schemes 16-17 or the adsorption desulfurization reaction apparatus of any one of schemes 18-21, wherein the process comprises: contacting a sulfur-containing hydrocarbon feedstock and an adsorption desulfurization catalyst in the reaction zone of the fluidized bed reactor to remove at least a portion of sulfur element in the hydrocarbon feedstock; and subjecting the obtained hydrocarbon-catalyst mixture successively to separation in the settling zone, the airflow particle sorter, the optional catalyst fine powder catcher, and the optional fine powder classificator to obtain hydrocarbon products and a spent catalyst.

23. The adsorption desulfurization process of scheme 22, wherein the contact of the sulfur-containing hydrocarbon feedstock and the adsorption desulfurization catalyst is conducted in an atmosphere containing hydrogen gas.

24. The adsorption desulfurization process of any one of schemes 22-23, wherein the molar ratio of hydrogen gas to the sulfur-containing hydrocarbon feedstock is 0.1-2:1, preferably 0.15-1.5:1, more preferably 0.2-1:1.

25. The adsorption desulfurization process of any one of schemes 22-24, wherein the conditions for contacting include: the temperature is 300-500° C., preferably 320-480° C.; the pressure by gauge in the fluidized bed reactor is 5-50 atm, preferably 10-45 atm; the weight hourly space velocity of the sulfur-containing hydrocarbon feedstock is 1-15 h$^{-1}$, preferably 2-12 h$^{-1}$; and the density of the catalyst dense bed in the fluidized bed reactor is 100-700 kg/m$^3$, preferably 150-500 kg/m$^3$.

26. The adsorption desulfurization process of any one of schemes 22-25, wherein the ratio of the inlet linear velocity of the hydrocarbon-catalyst mixture coming from the settling zone at the directing-intake port of the airflow particle sorter to the inlet linear velocity of the hydrocarbon-catalyst mixture in the sorter main body at the directing-outtake port is 1:1.2-2.5, preferably 1:1.5-2.

27. The adsorption desulfurization process of any one of schemes 22-26, wherein the inlet linear velocity of the hydrocarbon-catalyst mixture coming from the settling zone at the directing-intake port of the airflow particle sorter can be 0.8-10 m/s, preferably 1-8 m/s, more preferably 1.5-5 m/s; the inlet linear velocity of the hydrocarbon-catalyst mixture in the sorter main body of the airflow particle sorter at the directing-outtake port is 1.5-16 m/s, preferably 2-12 m/s, more preferably 2.5-10 m/s.

SPECIFIC MODE FOR CARRYING OUT THE INVENTION

Hereinafter, the present invention will be described in details by giving some specific embodiments. However, it should be understood that these embodiments are only for explaining and illustrating the present invention and is not intended to limit the present invention in any way.

Airflow Particle Sorter

Figure 1:
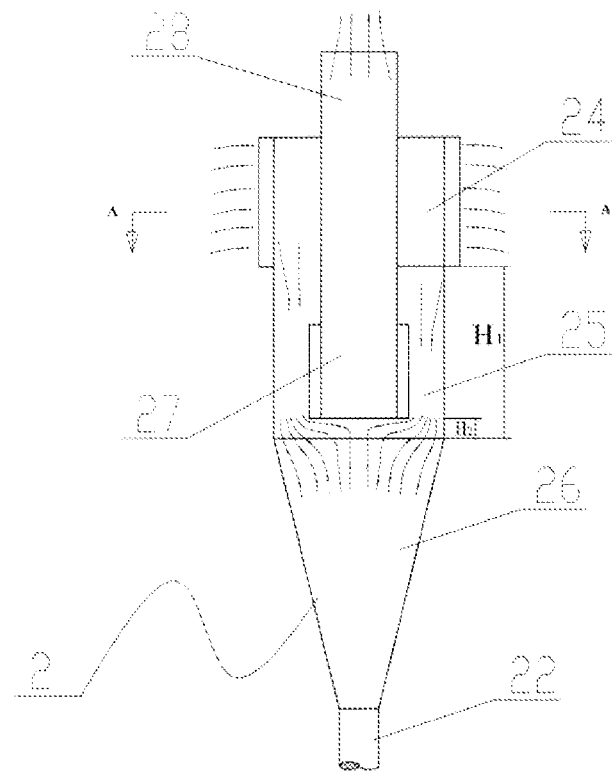
FIG. 1 is an illustration of the airflow particle sorter of the present invention.
Figure 2:
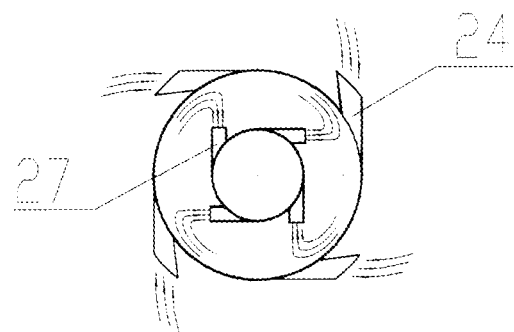
FIG. 2 is a projection in the A-A direction as shown in FIG. 1.

With reference to FIGS. 1 and 2, the airflow particle sorter of the present invention will be described in details. The airflow particle sorter includes a top-sealed sorter main body with a hollow structure, a discharge port 22, an outtake tube 28 and at least one directing-intake port 24; the inner space of the sorter main body, from the above to the bottom, includes, a straight tube zone 25 and a cone zone 26, the conical bottom of the cone zone 26 is connected to the straight tube zone 25; the discharge port 22 is located at the bottom of the cone zone 26; the directing-intake port 24 is installed in the upper part of the straight tube zone 25 in a tangential direction of the straight tube zone 25 (the upper part means, from the top to the bottom, the first 1/10, 2/10, 3/10, 4/10, 5/10 of the straight tube zone 25 in length), and is communicated with the inner space of the sorter main body;

the outtake tube 28 is hermetically inserted into the top of the sorter main body, and extends downward to the lower part of the straight tube zone 25 (the lower part means, from the bottom to the top, the first 1/10, 2/10, 3/10, 4/10, 5/10 of the straight tube zone 25 in length), the outtake tube 28 has a sealed bottom end; the lower part of the outtake tube 28 (the lower part means, from the bottom to the top, the first 1/10, 2/10, 3/10, 4/10, 5/10 of the outtake tube 28 in length) is installed with at least one directing-outtake port 27, which communicates the outtake tube 28 with the inner space of the sorter main body, the directing-outtake port 27 is installed in a tangential direction of the outtake tube 28.

In an embodiment of the airflow particle sorter, at least one internal such as stationary spinner vane is optionally present in the sorter main body. In another embodiment of the airflow particle sorter, none of internal such as stationary spinner vane is present in the sorter main body. In another embodiment of the airflow particle sorter, at least one internal such as stationary spinner vane is present in the sorter main body.

In an embodiment of the airflow particle sorter, the ratio of the length of the portion of the outtake tube 28 inserting into the sorter main body (i.e. the distance from the top of the sorter main body to the bottom of the outtake tube 28) to the length of the straight tube zone 25 is 0.6-1, e.g. 0.7-1, 0.8-1, 0.9-1, or 0.95-1.

In an embodiment of the airflow particle sorter, the cone zone 26 is present in a form of an inverse truncated cone.

In an embodiment of the airflow particle sort, the top of the directing-intake port aligns with the top of the straight tube zone.

In an embodiment of the airflow particle sort, the ratio of the height of the directing-intake port to the height of the directing-outtake port is 1/10 to 10/1, e.g. 1/5 to 5/1, 1/4 to 4/1, 1/3 to 3/1, 1/2 to 2/1, or 1:1; where if the number of the directing-intake port is more than one, said more than one directing-intake ports have the same size; and where if the number of the directing-outtake port is more than one, said more than one directing-outtake ports have the same size.

In the airflow particle sorter, the ratio of the height of the straight tube zone to the height of the cone zone can be 0.4-1.5:1, e.g. 0.5-1:1, such as 0.6-0.8:1.

The directing-intake port is installed in a tangential direction of the straight tube zone. In one hand, the directing-intake port provides an inlet for the hydrocarbon-catalyst mixture coming from the settling zone to enter the inner space of the airflow particle sorter, and in the other hand provides a driving force for the hydrocarbon-catalyst mixture coming from the settling zone to form a centrifugal force field in the inner space of the airflow particle sorter.

The directing-outtake port is installed in a tangential direction of the outtake tube. In one hand, the directing-outtake port provides an outlet for the hydrocarbon-catalyst mixture in the airflow particle sorter to exit the inner space of the airflow particle sorter, and in the other hand provides a driving force for the hydrocarbon-catalyst mixture to form a centrifugal force field in the inner space of the airflow particle sorter.

The number of the directing-intake port and the number of the directing-outtake port are respectively at least one, e.g. respectively can be 1-10. Preferably, the number of the directing-intake port and the number of the directing-outtake port are respectively more than one, which can form uniform and stable gas streams in both the straight tube zone and the outtake tube, and therefore further improve the separation and sorting efficiency of the present invention. More preferably, the number of the directing-intake port and the number of the directing-outtake port are respectively 2-8. The number of the directing-intake port and the number of the directing-outtake port can be identical or different, preferably identical.

In case that the number of the directing-intake port is more than one, the more than one directing-intake ports are preferably distributed in the circumferential direction of the straight tube zone, preferably equal interval. In case that the number of the directing-outtake port is more than one, the more than one directing-outtake ports are preferably distributed in the circumferential direction of the outtake tube, preferably equal interval. More than one directing-intake ports and more than one directing-outtake ports are oriented so that the hydrocarbon-catalyst mixture can form a rotating flow field with the same flow direction in the inner space of the sorter main body.

The directing-intake port and the directing-outtake port are spaced enough so that catalyst particles with larger particle size can be separated out. From the view of further improving the separation and sorting efficiency, the distance from the lower edge of the directing-intake port (in case of more than one directing-intake ports, means the lowest edge) to the bottom of the straight tube zone is H1, the distance from the lower edge of the directing-outtake port (in case of more than one directing-intake ports, means the lowest edge) to the bottom of the straight tube zone is H2, the ratio of H1/H2 can be 1:0.1-0.8, preferably 1:0.2-0.6.

The directing-intake port is installed in the upper part of the straight tube zone, preferably the upper edge of the directing-intake port is aligned with the top of the straight tube zone. The directing-outtake port is installed in the lower part of the outtake tube, preferably the lower edge of the directing-outtake port is aligned with the bottom of the outtake tube.

The cross-section areas perpendicular to the airflow direction of the directing-intake port and of the directing-outtake port (the horizontal cross-section areas) can be suitably chosen according to the throughput of the fluidized bed reactor. In addition, the adjustment of the cross-section areas perpendicular to the airflow direction of the directing-intake port and of the directing-outtake port is an adjustment of the flow rate of the hydrocarbon-catalyst mixture in the airflow particle sorter, and therefore is one of important means to control the size of catalyst particles returning to the reaction zone. Meanwhile, during the sorting of solid particles in a gas stream entraining solid particles (e.g. during the sorting of catalyst particles in the hydrocarbon-catalyst mixture coming from the settling zone), controlling the flow rate to a suitable level can further decrease the probability for crushing solid particles (such as catalyst particles) during the sorting. According to the present invention, the difference between the horizontal cross-section area of the straight tube zone and the horizontal cross-section area of the outtake tube is A0, the total cross-section area perpendicular to the airflow direction of the directing-intake port is A1, the total cross-section area perpendicular to the airflow direction of the directing-outtake port is A2, A1/A0 is preferably 0.01-0.8:1, more preferably 0.02-0.6:1; A2/A0 is preferably 0.01-0.5:1, more preferably 0.015-0.4:1. In case that the number of the directing-intake port is one, the total cross-section area perpendicular to the airflow direction of the directing-intake port means the area of the cross-section perpendicular to the airflow direction of the directing-intake port; and in case that the number of the directing-intake port is more than one, the total cross-section area perpendicular to the airflow direction of the directing-intake port means the sum of the areas of the cross-sections perpendicular to the airflow direction of the more than one directing-intake ports. In case that the number of the directing-outtake port is one, the total cross-section area perpendicular to the airflow direction of the directing-outtake port means the area of the cross-section perpendicular to the airflow direction of the directing-outtake port; and in case that the number of the directing-outtake port is more than one, the total cross-section area perpendicular to the airflow direction of the directing-outtake port means the sum of the areas of the cross-sections perpendicular to the airflow direction of the more than one directing-outtake ports.

The cross-section area of the outtake tube can be chosen suitably according to the inner space of the sorter main body. From the viewpoint of further improving the efficiency of separating and sorting catalyst particles with larger particle size in the hydrocarbon-catalyst mixture and further decreasing the probability for crushing catalyst particles during the separation and sorting, the ratio of the cross-section area perpendicular to the airflow direction of the outtake tube to the horizontal cross-section area of the straight tube zone is preferably 0.01-0.7:1, more preferably 0.04-0.6:1.

The separation of a gas stream entraining solid particles with the airflow particle sorter of the present invention can effectively separate and sort solid particles with larger particle size, merely entraining a small amount of fine powder; and during the separation, there is a low probability for crushing solid particles. Therefore, the airflow particle sorter of the present invention is particularly suitable as a built-in sorter for separating the gas stream entraining catalyst particles.

Adsorption Desulfurization Reaction Apparatus

The present invention provides an adsorption desulfurization reaction apparatus, which apparatus comprises a fluidized bed reactor, a catalyst regenerator, a catalyst reducer, an optional catalyst fine powder catcher, and an optional fine powder classificator.

The fluidized bed reactor comprises a top-sealed reactor main body, at least one airflow particle sorter and at least one stream inlet. The inner space of the reactor main body, from the above to the bottom, includes, a settling zone and a reaction zone, and the stream inlet is located at the bottom of the reaction zone.

According to the present invention, the reaction zone means a space for contacting and reacting the reactants (such as a sulfur-containing hydrocarbon feedstock) and an adsorption desulfurization catalyst, and the settling zone means a space for holding the hydrocarbon-catalyst mixture coming from the reaction zone, settling catalyst particles with larger particle size in the hydrocarbon-catalyst mixture and returning these catalyst particles to the reaction zone.

The reaction zone can be a straight tube reaction zone, or can be a variable diameter reaction zone, preferably a variable diameter reaction zone, more preferably a variable diameter cylindrical reaction zone. From the viewpoint of further improving the adsorption desulfurization effect, various internals that are conventionally used in the art for strengthening the contact between the gas phase and the liquid phase can be installed in the reaction zone.

The shape of the settling zone can be a conventionally chosen shape under the premise that the catalyst particles with larger particle size can settle and return to the reaction zone.

The airflow particle sorter is the airflow particle sorter as provided in the present invention, the sorter main body of the airflow particle sorter is located in the settling zone, the outtake tube hermetically passes through the top of the fluidized bed reactor, the directing-intake port is communicated with the settling zone, the discharge port downward extends into the reaction zone.

The gas stream coming from the settling zone comes into the sorter main body of the airflow particle sorter via the directing-intake port of the airflow particle sorter and is subjected to the sorting. The sorted catalyst particles with larger particle size return to the reaction zone via the discharge port of the airflow particle sorter, the remaining gas stream is sent out of the fluidized bed reactor via the outtake tube of the airflow particle sorter.

The structure of the airflow particle sorter has been discussed in detailed hereinbefore, and will not be further discussed here.

Figure 3:
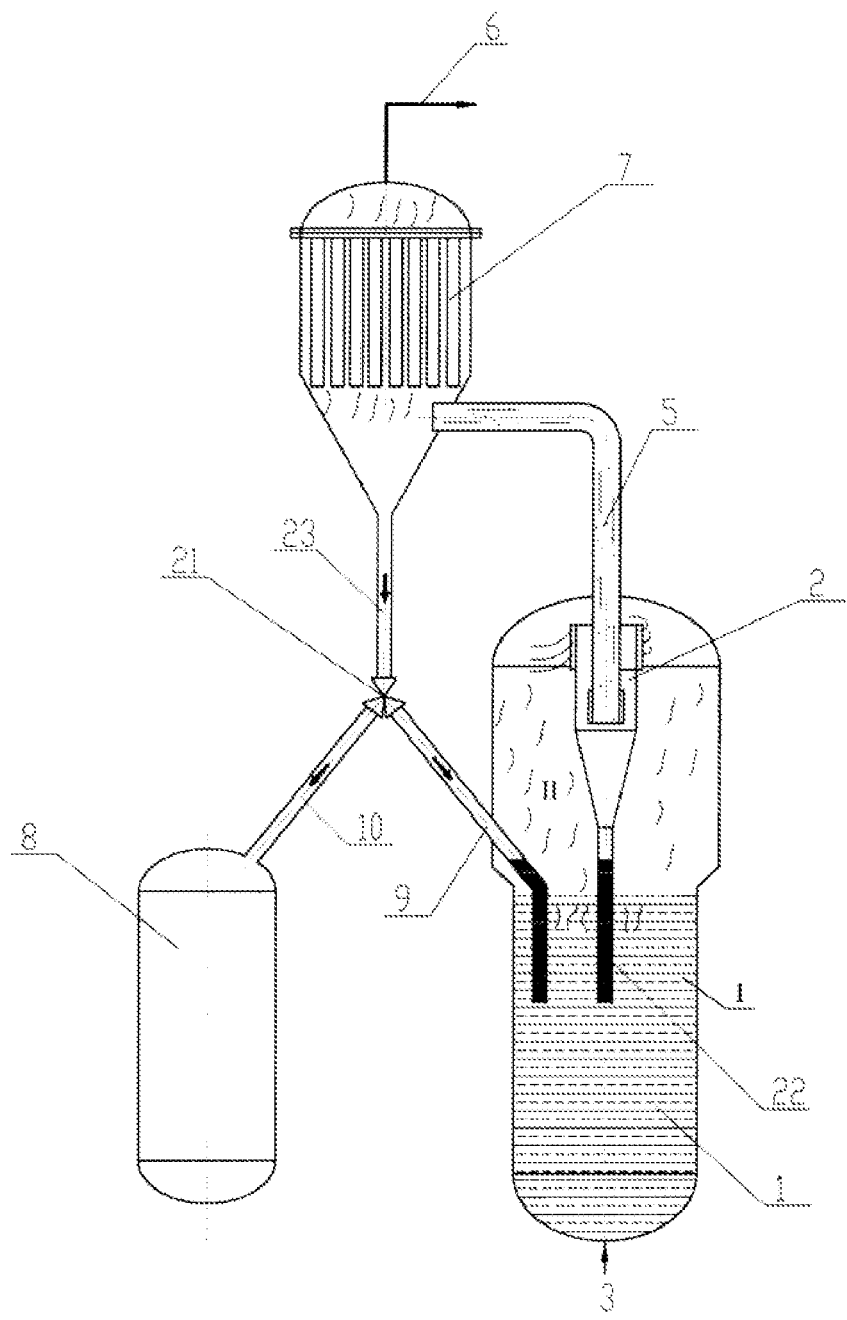
FIG. 3 is an illustration for an embodiment of the fluidized bed reactor of the present invention.
Figure 4:
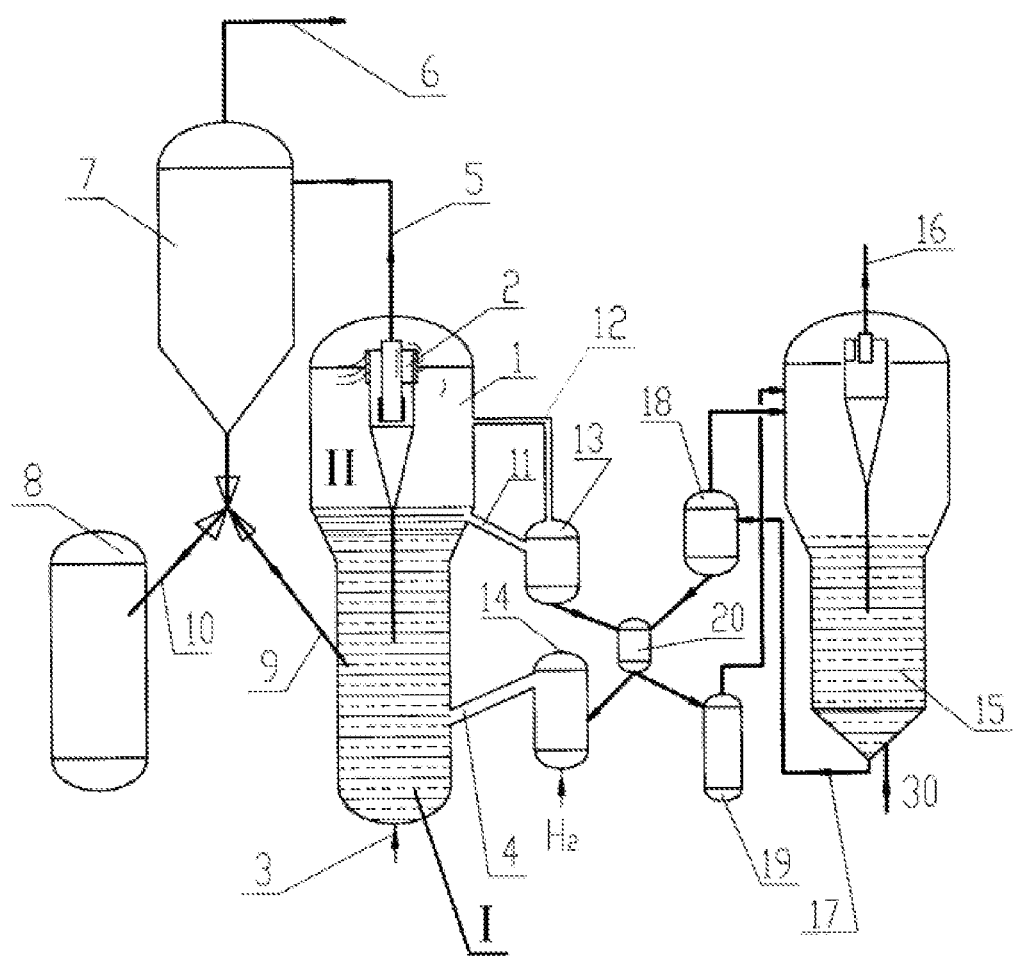
FIG. 4 is an illustration for another embodiment of the fluidized bed reactor of the present invention.

With reference to FIGS. 3 and 4, the adsorption desulfurization reaction apparatus of the present invention will be described hereinafter.

As shown in FIG. 3 or FIG. 4, the adsorption desulfurization reaction apparatus of the present invention, the sorter main body of the airflow particle sorter 2 is located in the settling zone II of the fluidized bed reactor 1, the outtake tube of the airflow particle sorter 2 hermetically passes through the top of the fluidized bed reactor 1, the directing-intake port of the airflow particle sorter 2 is communicated with the settling zone II, the discharge port 22 of the airflow particle sorter 2 extends downwardly to the reaction zone I of the fluidized bed reactor 1. In use, the hydrocarbon-catalyst mixture coming from the settling zone II enters the sorter main body of the airflow particle sorter 2 via the directing-intake port of the airflow particle sorter 2 and is subjected to the sorting, the sorted catalyst particles having larger particle size returns the reaction zone via the discharge port 22 of the airflow particle sorter 2, the remaining hydrocarbon-catalyst mixture is sent out of the fluidized bed reactor 1 via the outtake tube of the airflow particle sorter 2.

The number of the airflow particle sorter installed in the inner space of the reactor main body can be suitably chosen according to the throughput of the fluidized bed reactor under the premise that the hydrocarbon-catalyst mixture produced in the adsorption desulfurization can be duly subjected to the separation and the separated hydrocarbon product can be sent out of the reactor. From the viewpoint of further decreasing the probability for crushing catalyst particles during the separation, the ratio of the total cross-section area perpendicular to the airflow direction of the directing-intake port of the airflow particle sorter to the horizontal cross-section area of the settling zone can be 0.01-0.4:1, preferably 0.05-0.3:1. In case that the number of the airflow particle sorter is one, the total cross-section area perpendicular to the airflow direction of the directing-intake port means the total cross-section area perpendicular to the airflow direction of the directing-intake port installed on the airflow particle sorter; In case that the number of the airflow particle sorter is more than one, the total cross-section area perpendicular to the airflow direction of the directing-intake port means the total cross-section area perpendicular to the airflow direction of directing-intake ports installed on the more than one airflow particle sorter.

According to the adsorption desulfurization reaction apparatus of the present invention, from the viewpoint of further decreasing the amount of the fine catalyst powder entrained in the hydrocarbon product and improving the recovery of the catalyst, as shown in FIGS. 3 and 4, the adsorption desulfurization reaction apparatus preferably further comprises a catalyst fine powder catcher 7 installed out of the reactor main body. The feed port of the catalyst fine powder catcher 7 is communicated with the outtake tube of the airflow particle sorter 2. The catalyst fine powder catcher 7 is for capturing the fine catalyst powder entrained in the mixture from the outtake tube of the airflow particle sorter 2.

Figure 5:
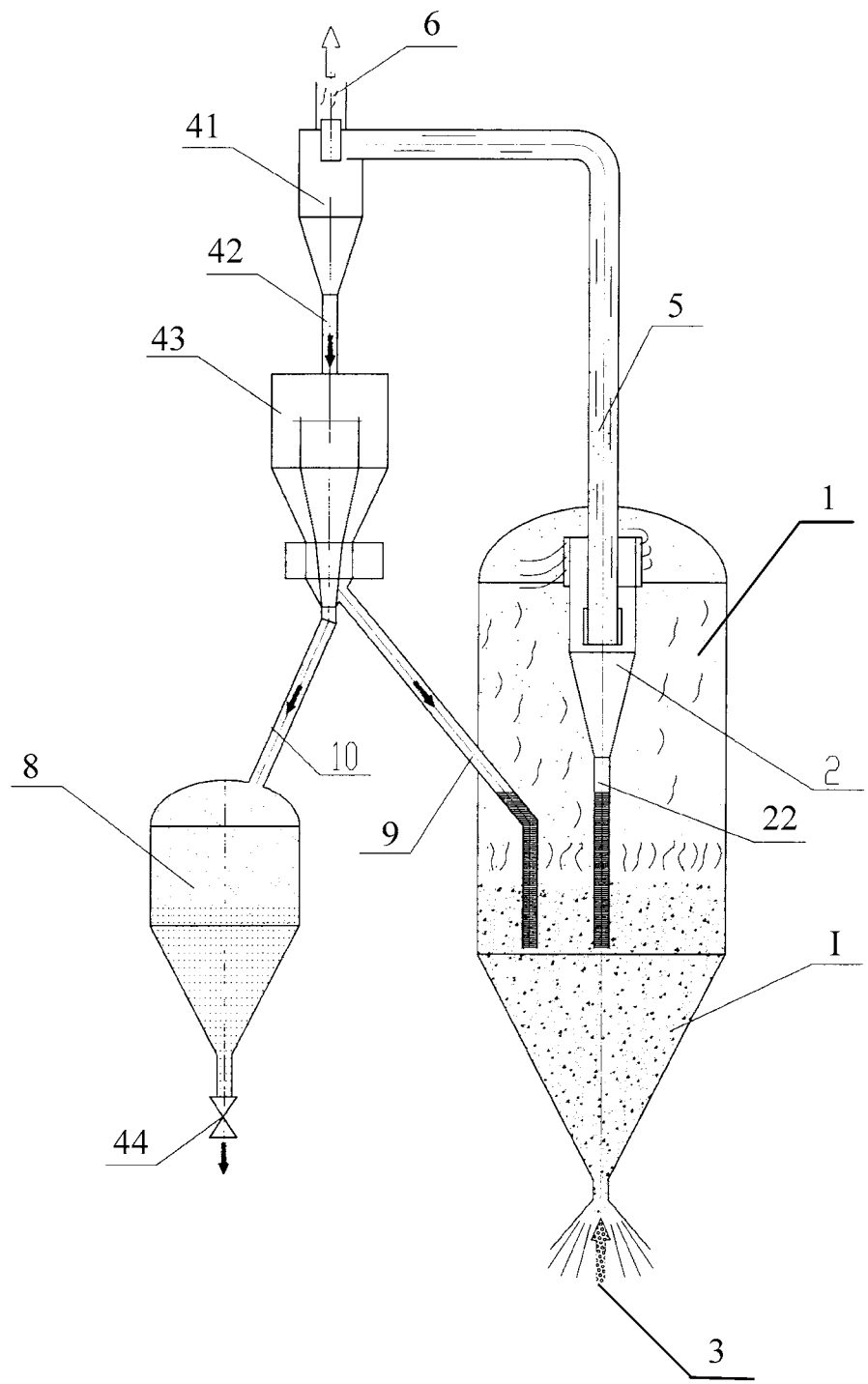
FIG. 5 is an illustration of the fluidized bed reactor of the present invention.

The catalyst fine powder catcher 7 can be any conventional catalyst fine powder catcher capable of achieving the above function, preferably a fine powder filter, for example, a high temperature filter composed of multi-metal filtering tubes. The metal filtering tubes have a through-hole structure. In use, the gas stream from the outtake tube of the airflow particle sorter 2 enters the metal filtering tubes via through-holes on the metal filtering tubes, while the fine catalyst powder is blocked by the metal filtering tubes. When the resistance drop between the inside and the outside of the filtering tubes reaches a certain value, a compressed air is blown back into the filtering tubes in pulse to remove the dust agglomerated on the filtering tube walls by the shock due to blowing back. The metal filtering tube and the compressed air pulse system are commercially available, and are not discussed herein in details. In another embodiment, the catalyst fine powder catcher can also be a cyclone separator (as shown in FIG. 5 and will be explained hereinafter).

The feed port of the catalyst fine powder catcher 7 can be connected to the outtake tube of the airflow particle sorter 2 with any conventional means so that the hydrocarbon mixture from the outtake tube of the airflow particle sorter 2 is sent to the catalyst fine powder catcher 7 to be subjected to the separation. As shown in FIGS. 3 and 4, the outtake tube of the airflow particle sorter 2 and the feed port of the catalyst fine powder catcher 7 can be connected with a connecting tube 5.

The hydrocarbon product 6 obtained by separation in the catalyst fine powder catcher 7 can be sent to a subsequent refining and processing unit to be subjected to a further treatment. The fine catalyst powder obtained by separation in the catalyst fine powder catcher 7 is discharged from the solid phase discharge tube 23 of the catalyst fine powder catcher 7. The discharged fine catalyst powder can enter the catalyst fine powder storage tank 8 via the tube 10. According to the requirement for the catalyst particle size distribution in the fluidized bed reactor, a part of the recovered fine catalyst powder is sent back to the fluidized bed reactor via the tube 9.

In an embodiment of the present invention, the catalyst fine powder catcher comprises a second discharge tube 9, the second discharge tube 9 is connected to the solid phase discharge tube 23 and hermetically passes through the side wall of the reactor main body, inserts into the reactor main body and extends into the reaction zone so that a part of the separated catalyst particles are sent to the reaction zone.

Specifically, as shown in FIG. 3, the hydrocarbon mixture from the outtake tube of the airflow particle sorter 2 is sent to the catalyst fine powder filter 7 via the connecting tube 5 to obtain the fine catalyst powder by separation, wherein, the obtained hydrocarbon product 6 is discharged from the top of the catalyst fine powder filter 7 and sent to the subsequent refining and processing unit; the obtained fine catalyst powder is, via the solid phase discharge tube 23 of the catalyst fine powder filter 7, through a two-way valve 21, sent from the conveying tube 10 to the catalyst fine powder storage tank 8 and/or reintroduced from the conveying tube 9 into the reaction zone I. By adjusting the two-way valve 21, the amount of the catalyst sent to the catalyst fine powder storage tank 8 and the amount or the particle size of the catalyst reintroduced into the reaction zone can be adjusted.

According to the adsorption desulfurization reaction apparatus of the present invention, the solid phase stream from the solid phase discharge tube of the catalyst fine powder catcher can also be sent to a high-precision classificator to classify the fine catalyst powder captured in the catalyst fine powder catcher, wherein the catalyst with a higher particle size is reintroduced into the reaction zone of the fluidized bed reactor, and the catalyst with a smaller particle size is discharged. This can further decrease the accumulated amount of the fine powder catalyst in the fluidized bed reactor, and also can further improve the catalyst utility and further reduce the catalyst consumption.

In a preferable embodiment of the present invention, the discharge port of the catalyst fine powder catcher is communicated with a feed port of the fine powder classificator; the fine powder classificator comprises a second discharge tube for receipt of larger catalyst particles sorted out by the fine powder classificator, wherein the second discharge tube hermetically passes through the side wall of the reactor main body, inserts into the reactor main body and extends into the reaction zone.

The fine powder classificator can be any conventional classificator that can classify the fine powder based on particle sizes, e.g. a high-precision fine powder classificator.

Specifically, as shown in FIG. 5, the solid phase stream from the leg 42 of the cyclone separator 41 enters the fine powder classificator 43 to be subjected to a further separation. The sorted smaller catalyst particles are sent to the catalyst fine powder storage tank 8 via the third discharge tube 10, and regularly discharged via the valve 44 if necessary. The sorted larger catalyst particles are sent to the reaction zone of the fluidized bed reactor via the second discharge tube 9.

The selection of a suitable fine powder classificator and the adjustment of its operation condition to separate and sort the solid particles with a predetermined particle size are well within the knowledge of a skilled person in the art and can be determined by a limited number of experiments, and therefore will not be discussed in details.

In the fluidized bed reactor of the present invention, the airflow particle sorter of the present invention is used as a built-in sorter, and can effectively separate out larger particles. Moreover, during the separation, there is a low probability for crushing solid particles. Therefore, the fluidized bed reactor of the present invention is particularly suitable as an adsorption desulfurization reactor for hydrocarbon feedstock.

Therefore, the present invention provides the use of the fluidized bed reactor of the present invention as the adsorption desulfurization reactor for hydrocarbon feedstock. In case that the fluidized bed reactor of the present invention is used as the adsorption desulfurization reactor for hydrocarbon feedstock, the hydrocarbon feedstock kind and the adsorption desulfurization condition are not particularly limited, and can be those conventionally used in the art.

The fluidized bed reactor of the present invention can be communicated with a regenerator for the spent catalyst (i.e. a catalyst regenerator) and a reducer for the regenerated catalyst (i.e. a catalyst reducer) to conduct the adsorption desulfurization of the sulfur-containing hydrocarbon feedstock. The hydrocarbon product and the spent catalyst are separated from the obtained hydrocarbon-catalyst mixture, and the spent catalyst is subjected to regeneration and reduction. A continuous operation of the apparatus can be achieved.

According to the adsorption desulfurization reaction apparatus of the present invention, as shown in FIG. 4, the adsorption desulfurization reaction apparatus further comprises the catalyst regenerator 15 and the catalyst reducer 14, wherein the catalyst regenerator 15 is used for regenerating the spent catalyst, and the catalyst reducer 14 is used for reducing the regenerated catalyst to recover its catalytic activity. The catalyst regenerator and the catalyst reducer can be communicated with the inner space of the fluidized bed reactor with the conventional means, so that the spent catalyst is convey to the catalyst regenerator to be subjected to the regeneration, and the reduced catalyst is recycled to the reaction zone of the fluidized bed reactor.

Specifically, as shown in FIG. 4, the spent catalyst receiving tank 13 can be mounted. The spent catalyst is conveyed via the spent catalyst conveying tube 11 to the spent catalyst receiving tank 13; the spent catalyst receiving tank 13 is connected to the regenerator feed buffering tank 19 with the lock hopper 20; and the spent catalyst is sent to the catalyst regenerator 15 via the regenerator feed buffering tank 19 to be subjected to the regeneration. The regenerated catalyst enters the regenerated catalyst receiver 18, and enters the catalyst reducer 14 via the lock hopper 20 to be subjected to the regeneration. The resulting reduced catalyst is recycled to the reaction zone I of the fluidized bed reactor 1 via a reduced catalyst conveying tube 4.

The upper part of the spent catalyst receiving tank is connected to the fluidized bed reactor via the catalyst conveying tube, and the lower part thereof is connected to the lock hopper. From the viewpoint of improving the smoothness of the spent catalyst entering the spent catalyst receiving tank, as shown in FIG. 4, it is preferable that the gas conveying tube 12 is installed on the top of the spent catalyst receiving tank 13, and connected to the settling zone II of the fluidized bed reactor 1, so that the inner space of the spent catalyst receiving tank 13 is communicated with the settling zone of the fluidized bed reactor 1.

Adsorption Desulfurization Process

The present invention also provides an adsorption desulfurization process, which process is conducted in the adsorption desulfurization reaction apparatus provided in the present invention.

The adsorption desulfurization process of the present invention comprises: contacting a sulfur-containing hydrocarbon feedstock and an adsorption desulfurization catalyst in the reaction zone of the fluidized bed reactor to remove at least a portion of sulfur element in the hydrocarbon feedstock.

According to the present invention, the sulfur-containing hydrocarbon feedstock is not particularly limited, and can be any conventional sulfur-containing hydrocarbon feedstock for which the adsorption desulfurization is needed. Preferably, the sulfur-containing hydrocarbon feedstock is one or more of a straight-run gasoline, a catalytic gasoline and a coker gasoline.

The adsorption desulfurization catalyst can be any conventional adsorption desulfurization catalyst in the art, preferably an adsorption desulfurization catalyst with zinc oxide being as active component.

The particle size of the adsorption desulfurization catalyst can be conventionally selected, under the premise that the fluidization can be accomplished. In generally, the particle size of the adsorption desulfurization catalyst can be 20-150 µm. According to the present invention, the particle size of the catalyst is the volume-average particle size, and is determined with a laser particle size analyzer.

According to the process of the present invention, the contact of the sulfur-containing hydrocarbon feedstock and the adsorption desulfurization catalyst is conducted in an atmosphere containing hydrogen gas. Hydrogen gas and the sulfur-containing hydrocarbon feedstock are fed together from the feed port at the bottom of the fluidized bed reactor to the reaction zone of the fluidized bed reactor. The used amount of hydrogen gas can be conventionally chosen. In general, in the feedstock to the fluidized bed reactor, the molar ratio of hydrogen gas to the sulfur-containing hydrocarbon feedstock can be 0.1-2:1, preferably 0.15-1.5:1, more preferably 0.2-1:1. According to the process of the present invention, the conditions for contacting the sulfur-containing hydrocarbon feedstock and the adsorption desulfurization catalyst are not particularly limited, and can be conventionally chosen, under the premise that the sulfur element present in the sulfur-containing hydrocarbon feedstock can be decreased to the regulation level. In general, the contact temperature can be 300-500° C., preferably 320-480° C.; the pressure by gauge in the fluidized bed reactor can be 5-50 atm, preferably 10-45 atm; the weight hourly space velocity of the sulfur-containing hydrocarbon feedstock can be 1-15 $h^{-1}$, preferably 2-12 $h^{-1}$. According to the process of the present invention, from the viewpoint of strengthening the desulfurization effect, the density of the catalyst dense bed in the fluidized bed reactor is preferably 100-700 $kg/m^3$, more preferably 150-500 $kg/m^3$.

The process of the present invention further comprises separating the obtained hydrocarbon-catalyst mixture successively in the settling zone, the airflow particle sorter, the optional catalyst fine powder catcher, and the optional fine powder classificator to obtain the hydrocarbon product and the spent catalyst.

The hydrocarbon-catalyst mixture obtained from the reaction zone upwardly enters the settling zone. In the settling zone, the apparent velocity of the hydrocarbon-catalyst mixture decreases and the carrying capability decreases. A part of the catalyst particles with larger particle size settles by the action of gravity and returns to the reaction zone. The remaining hydrocarbon-catalyst mixture enters the inner space of the sorter main body via the directing-intake port of the airflow particle sorter to be subjected to the separation and sorting. The particles with larger particle size are separated and returns to the catalyst dense bed of the reaction zone via the discharge port of the airflow particle sorter. The obtained hydrocarbon mixture is discharged as hydrocarbon product or sent to the catalyst fine powder catcher to be subjected to the further separation to produce the hydrocarbon product and the fine catalyst powder. In case that fine catalyst particles in the reactor bed are below the normal level, a part of the fine catalyst powder can be reintroduced to the reaction zone of the fluidized bed reactor. Preferably, the fine catalyst powder from the catalyst fine powder catcher can be separated and sorted in the fine powder classificator to produce catalyst particles with larger particle size and catalyst particles with smaller particle size, and a part or all of catalyst particles with larger particle size are reintroduced to the reaction zone of the fluidized bed reactor.

According to the process of the present invention, because the hydrocarbon-catalyst mixture is sent out of the fluidized bed reactor with the airflow particle sorter, the hydrocarbon-catalyst mixture is separated and sorted by the combined action of the centrifugal force caused by the stable rotary gas flow field, the viscous force caused by the gas applying to catalyst particles, and the gravity in the airflow particle sorter to produce catalyst particles with larger particle size and catalyst particles with smaller particle size, therefore a population of particles having a special particle size can be separated and sorted by controlling the inlet linear velocities at the directing-intake port and at directing-outtake port of the streams.

According to the process of the present invention, upon using the adsorption desulfurization reaction apparatus provided in the present invention, the ratio of the inlet linear velocity of the hydrocarbon-catalyst mixture coming from the settling zone at the directing-intake port of the airflow particle sorter to the inlet linear velocity of the hydrocarbon-catalyst mixture in the sorter main body at the directing-outtake port can be 1:1.2-2.5, preferably 1:1.5-2.

Under the premise that catalyst particles with a specific particle size can be separated, from the viewpoint of further decreasing the probability for secondarily crushing the catalyst during the separation and sorting, the inlet linear velocity of the hydrocarbon-catalyst mixture coming from the settling zone at the directing-intake port of the airflow particle sorter can be 0.8-10 m/s, preferably 1-8 m/s, more preferably 1.5-5 m/s; the inlet linear velocity of the hydrocarbon-catalyst mixture in the sorter main body of the airflow particle sorter at the directing-outtake port can be 1.5-16 m/s, preferably 2-12 m/s, more preferably 2.5-10 m/s.

In an embodiment of the present invention, the inlet linear velocity of the hydrocarbon-catalyst mixture coming from the settling zone at the directing-intake port of the airflow particle sorter is 0.8-10 m/s, and the inlet linear velocity of the hydrocarbon-catalyst mixture in the sorter main body of the airflow particle sorter at the directing-outtake port is 1.5-16 m/s.

In a preferable embodiment of the present invention, the inlet linear velocity of the hydrocarbon-catalyst mixture coming from the settling zone at the directing-intake port of the airflow particle sorter is 1-8 m/s, and the inlet linear velocity of the hydrocarbon-catalyst mixture in the sorter main body of the airflow particle sorter at the directing-outtake port is 2-12 m/s.

In a more preferable embodiment of the present invention, the inlet linear velocity of the hydrocarbon-catalyst mixture coming from the settling zone at the directing-intake port of the airflow particle sorter is 1.5-5 m/s, and the inlet linear velocity of the hydrocarbon-catalyst mixture in the sorter main body of the airflow particle sorter at the directing-outtake port is 2.5-10 m/s.

The inlet linear velocity at the directing-intake port is the ratio of the volume flow rate of the gas stream taken out from the airflow particle sorter to the total cross-section area perpendicular to the airflow direction of the directing-intake port, and the inlet linear velocity at the directing-outtake port is the ratio of the volume flow rate of the gas stream taken out from the airflow particle sorter to the total cross-section area perpendicular to the airflow direction of the directing-outtake port.

According to the process of the present invention, the catalyst having a particle size of >20 μm, preferably >25 μm and more preferably >30 μm can be separated and sent back to the reaction zone.

The velocity of the hydrocarbon-catalyst mixture at the directing-intake port of the airflow particle sorter and the velocity of the hydrocarbon-catalyst mixture at the directing-outtake port of the airflow particle sorter can be adjusted by the adjustment of the pressure or the reaction stream throughout in the fluidized bed reactor.

According to the process of the present invention, it is preferable that the fine catalyst powder having the particle size sufficient to meet the requirement of the fluidized bed reactor is separated from the fine catalyst powder coming from the catalyst fine powder catcher with the fine powder classificator, and is reintroduced to the reaction zone of the fluidized bed reactor. The method of selecting the type of the fine powder classificator and adjusting its operation condition so that the fine catalyst powder having a pre-determined particle size can be separated is well known in the art, and will not be discussed in details herein.

The process of the present invention further comprises sending at least a part of the spent catalyst to the catalyst regenerator to be subjected to the regeneration, reducing the regenerated catalyst in the catalyst reducer, and recycling at least a part of the reduced catalyst to the reaction zone.

According to the present invention, the method of regenerating the spent catalyst is not particularly limited, and can be conventionally chosen. For example, the regeneration can be conducted according to the method as disclosed in CN1323137C. Specifically, the spent catalyst can be regenerated in an atmosphere containing oxygen gas. The condition for regeneration includes: the temperature can be 350-650° C.; the pressure, as absolute pressure, can be 240-1134 kPa; the apparent linear velocity of the oxygen-containing gas can be 0.3-1.5 m/s.

According to the present invention, the method of reducing the regenerated catalyst is not particularly limited. The regenerated catalyst can be reduced in a conventional condition. In general, the regenerated catalyst and the hydrogen (H2) containing gas can be contacted to reduce the regenerated catalyst. The condition for the reduction can be conventionally chosen. In general, the condition for the reduction includes: the temperature can be 300-550° C.; the pressure, as absolute pressure, can be 800-3000 kPa; the apparent linear velocity of the hydrogen-containing gas can be 0.1-2 m/s. Hydrogen gas is used in an amount sufficient to reduce the regenerated catalyst.

According to the process of the present invention, before sending the regenerated catalyst to the catalyst reducer to conduct the reduction, the catalyst is preferably stripped with nitrogen gas to remove oxygen gas entrained in the regenerated catalyst. The stripping can be conducted in the regenerated catalyst receiver. According to the present invention, the condition for stripping is not particularly limited, and can be conventionally chosen under the premise that oxygen gas entrained in the regenerated catalyst can be removed.

Hereinafter, with reference to FIG. 4, a preferable embodiment of the adsorption desulfurization process of the present invention will be described in detail.

The feedstock 3 containing a sulfur-containing hydrocarbon feedstock and hydrogen gas is sent to the reaction zone I of the fluidized bed reactor from the stream inlet of the fluidized bed reactor 1, and is contacted with the adsorption desulfurization catalyst to remove at least a part of the sulfur element in the sulfur-containing hydrocarbon feedstock.

The obtained hydrocarbon-catalyst mixture enters the settling zone II of the fluidized bed reactor. The catalyst particles with larger particle size settles by the action of gravity and return to the reaction zone I. The hydrocarbon-catalyst mixture coming from the settling zone II enters the airflow particle sorter 2 from the directing-intake port. Catalyst particles with larger particle size (e.g., catalyst particles with particle size of >20 μm, preferably >25 μm and more preferably >30 μm) are separated from the mixture and sent back to the reaction zone I of the fluidized bed reactor. The mixture discharged from the airflow particle sorter 2 enters the catalyst fine powder catcher 7 via the conveying tube 5 to produce the hydrocarbon product 6 by separation. The fine catalyst powder collected in the catalyst fine powder catcher 7 can be directly sent to the catalyst fine powder storage tank 8 via the conveying tube 10, and be exported as necessary. According to the requirement of the fluidized bed reactor on the catalyst particle size distribution, a part of the fine catalyst powder can be reintroduced to the reaction zone of the fluidized bed reactor via the conveying tube 9.

The spent catalyst in the reaction zone I of the fluidized bed reactor 1 enters the spent catalyst receiving tank 13 via the conveying tube 11, then the regenerator feed buffering tank 19 via the lock hopper 20, and finally the catalyst regenerator 15 to conduct the regeneration. The oxygen-containing gas 30 (such as a mixture containing oxygen gas and nitrogen gas) enters the bottom of the catalyst regenerator 15, and the gas 16 produced by regeneration leaves from the top of the catalyst regenerator 15.

The regenerated catalyst enters the regenerated catalyst receiver 18, and is stripped with the nitrogen gas 17 in the regenerated catalyst receiver 18 and then sent to the catalyst reducer 14 via the lock hopper 20 to conduct the reduction in an atmosphere containing hydrogen gas. The obtained reduced catalyst is reintroduced to the reaction zone I of the fluidized bed reactor 1 via the conveying tube 4.

EXAMPLES

The present invention will be illustrated by the following examples. It should be understood that the scope of the present invention is not limited by these examples.

In the examples, the sulfur-containing hydrocarbon feedstock was subjected to the adsorption desulfurization in the adsorption desulfurization reaction apparatus, as shown in FIG. 4, wherein The fluidized bed reactor was a straight tube reactor, its inner diameter was 120 mm, and the height of the inner space of the reactor was 3000 mm.

One airflow particle sorter was installed in the fluidized bed reactor. The height of the inner space of the sorter main body of the airflow particle sorter was 300 mm. The diameter of the straight tube zone was 70 mm. The ratio of the height of the straight tube zone to the height of the cone zone was 1:1.4.

A flow meter was mounted on the connecting tube 5 that connected the outtake tube of the airflow particle sorter and the feed port of the catalyst fine powder catcher to measure the volume flow rate (expressed as Q) of the hydrocarbon mixture taken out from the airflow particle sorter, and the linear velocity at the directing-intake port of the airflow particle sorter and the linear velocity at the directing-outtake port of the airflow particle sorter were calculated by the following formulae:

$$V_{directing\text{-}intake\ port}=Q/A_1;$$

$$V_{directing\text{-}outtake\ port}=Q/A_2;$$

$A_1$ was the total cross-section area perpendicular to the airflow direction of the directing-intake port; $A_2$ was the total cross-section area perpendicular to the airflow direction of the directing-outtake port.

In the following examples and comparative examples, the particle size and the average particle size were determined with the laser particle size analyzer purchased from Malvern Company, wherein the average particle size was the volume-average particle size.

In the following examples and comparative examples, the specific surface area and the pore volume (PV) of the catalyst were measured by the nitrogen adsorption static volumetric method.

Examples 1-4 are used to illustrate the present invention.

Example 1

In this example, the straight tube zone of the airflow particle sorter was installed with 4 directing-intake ports in its tangential direction (the directing-intake ports were distributed in the circumferential direction of the straight tube zone (as shown in FIG. 2), and each of the directing-intake ports had the same cross-section area perpendicular to the airflow direction); the outtake tube of the airflow particle sorter was installed with 4 directing-outtake ports in its tangential direction (the directing-outtake ports were distributed in the circumferential direction of the outtake tube (as shown in FIG. 2), and each of the directing-outtake ports had the same cross-section area perpendicular to the airflow direction); the difference between the horizontal cross-section area of the straight tube zone and the horizontal cross-section area of the outtake tube was $A_0$, the total cross-section area perpendicular to the airflow direction of the directing-intake port was $A_1$, the total cross-section area perpendicular to the airflow direction of the directing-outtake port was $A_2$, $A_1/A_0$ was 0.4:1, $A_2/A_0$ was 0.2:1; the ratio of the cross-section area perpendicular to the airflow direction of the outtake tube to the horizontal cross-section area of the straight tube zone was 0.3:1; the distance from the lower edge of the directing-intake port to the bottom of the straight tube zone was $H_1$, the distance from the lower edge of the directing-outtake port to the bottom of the straight tube zone was $H_2$, the ratio of H1/H2 was 1:0.3; the ratio of the total cross-section area perpendicular to the airflow direction of the directing-intake port to the horizontal cross-section area of the settling zone was 0.3:1.

The catalyst fine powder catcher used in this Example was a stainless steel filtering tube filter, wherein two stainless steel filtering tubes were installed in a cylindrical shell in parallel, the hydrocarbon-catalyst mixture from the airflow particle sorter was sent to the shell of the stainless steel filtering tube filter, the stainless steel filtering tube had an inner diameter of 80 mm and a length of 400 mm, the through-holes on the filtering tube had an average pore diameter of 0.2 μm; and the shell had an inner diameter of 240 mm.

The sulfur-containing hydrocarbon feedstock (being a sulfur-containing gasoline, its properties being listed in Table 2) and hydrogen gas, with a molar ratio of 0.2:1, were sent to the reaction zone of the fluidized bed reactor, and contacted with an adsorption desulfurization catalyst (produced by Sinopec Corp. Research Institute of Petroleum Processing, FCAS-R09, the properties of the regenerated catalyst being listed in Table 1) to remove at least a part of sulfur elements in the hydrocarbon feedstock, wherein the contacting temperature was 400° C., the pressure by gauge was 26 atm, and the weight hourly space velocity of the sulfur-containing hydrocarbon feedstock was 4 h$^{-1}$.

The resulting contacted hydrocarbon-catalyst mixture was sent through the settling zone into the airflow particle sorter, wherein the hydrocarbon-catalyst mixture had a linear velocity at the directing-intake port of the airflow particle sorter of 1.5 m/s, and a linear velocity at the directing-outtake port of the airflow particle sorter of 3 m/s.

The hydrocarbon-catalyst mixture from the airflow particle sorter was subjected to a further separation in the stainless steel filtering tube filter to produce the hydrocarbon product and the fine catalyst powder. The fine catalyst powder was sent to the catalyst fine powder storage tank, and the hydrocarbon product was sent to the subsequent refining and processing unit.

The spent catalyst was regenerated in the catalyst regenerator, the regenerated catalyst was sent to the catalyst reducer to conduct the reduction, and the reduced catalyst was reintroduced to the reaction zone of the fluidized bed reactor, wherein the condition for regeneration included: the temperature was 510° C.; the absolute pressure was 400 kPa; and the apparent linear velocity of the oxygen-containing gas was 0.45 m/s; the condition for reduction included: the temperature was 400° C.; the absolute pressure was 3000 kPa; and the apparent linear velocity of the hydrogen-containing gas was 0.4 m/s.

The reaction was continuously conducted for 500 hours. During the reaction, the composition of the obtained hydrocarbon product, the average particle size of the catalyst in the catalyst fine powder storage tank, and the average particle size of the catalyst in the catalyst dense bed of the fluidized bed reactor were monitored. The results were listed in Table 3. After 500 hours of reaction, in the catalyst in the dense bed of the fluidized bed reactor, the content of the catalyst having a particle size of less than 30 μm was 6.5 wt %. A total of 14.2 kg catalyst was charged into the fluidized bed reactor before the reaction, a total of 1.28 kg catalyst was supplemented to the fluidized bed reactor during the reaction; and 1.82 kg fine catalyst powder was collected in the catalyst fine powder storage tank after 500 hours.

TABLE 1

| | |
|---|---|
| Bulk density, g/cm$^3$ | 1.2498 |
| Specific surface area, m$^2$/g | 23 |
| PV, cm$^3$/g | 0.12 |
| Sulfur content, wt % | 4.72 |
| Char content, wt % | 0.53 |
| Particle size distribution, wt % | |
| 0-20 μm | 4.46 |
| 0-40 μm | 10.93 |
| Average particle size, μm | 68.89 |

TABLE 2

| | | |
|---|---|---|
| Density d 20° C./g · cm$^{-3}$ | | 0.7381 |
| Sulfur content/μg · g$^{-1}$ | | 295 |
| Olefin content/% | | 25.35 |
| Octane number | RON | 90.7 |
| | MON | 80.9 |
| Distillation range/° C. | Initial boiling point | 20.9 |
| | 5% | 29.9 |
| | 10% | 31.5 |
| | 30% | 55.6 |
| | 50% | 89.0 |
| | 70% | 137.1 |
| | 90% | 182.1 |
| | 95% | 199.6 |
| | Final boiling point | 228.3 |

TABLE 3

| | Time/h | | | | |
|---|---|---|---|---|---|
| | 100 | 200 | 300 | 400 | 500 |
| Sulfur content of the product/wppm | 4.5 | 3.2 | 5.8 | 4.6 | 3.4 |

TABLE 3-continued

| | Time/h | | | | |
|---|---|---|---|---|---|
| | 100 | 200 | 300 | 400 | 500 |
| Antiknock index reduction value* | 0.58 | 0.48 | 0.65 | 0.62 | 0.55 |
| Average particle size of the catalyst/μm — Fine powder storage tank | 15.3 | 15.3 | 14.8 | 16.2 | 16.7 |
| Catalyst dense bed | 70.5 | 67.9 | 69.5 | 66.7 | 64.5 |

*Based on the antiknock index of the sulfur-containing gasoline as hydrocarbon feedstock, wherein the antiknock index = (RON + MON)/2

Example 2

The adsorption desulfurization was conducted in the same manner as Example 1, except that $A_1/A_0$ was 0.24:1, $A_2/A_0$ was 0.15:1, the linear velocity of the hydrocarbon-catalyst mixture at the directing-intake port of the airflow particle sorter was 2.5 m/s, and the linear velocity at the directing-outtake port of the airflow particle sorter was 4 m/s.

The reaction was continuously conducted for 500 hours. During the reaction, the composition of the obtained hydrocarbon product, the average particle size of the catalyst in the catalyst fine powder storage tank, and the average particle size of the catalyst in the catalyst dense bed of the fluidized bed reactor were monitored. The results were listed in Table 4. After 500 hours of reaction, in the catalyst in the dense bed of the fluidized bed reactor, the content of the catalyst having a particle size of less than 30 μm was 9.5 wt %. A total of 14.2 kg catalyst was charged into the fluidized bed reactor before the reaction, a total of 1.34 kg catalyst was supplemented to the fluidized bed reactor during the reaction; and 1.88 kg fine catalyst powder was collected in the catalyst fine powder storage tank after 500 hours.

TABLE 4

| | Time/h | | | | |
|---|---|---|---|---|---|
| | 100 | 200 | 300 | 400 | 500 |
| Sulfur content of the product/wppm | 3.5 | 3.6 | 4.8 | 4.3 | 3.5 |
| Antiknock index reduction value | 0.55 | 0.38 | 0.62 | 0.65 | 0.58 |
| Average particle size of the catalyst/μm — Fine powder storage tank | 13.4 | 14.5 | 15.7 | 16.3 | 17.8 |
| Catalyst dense bed | 72.3 | 69.3 | 67.7 | 68.0 | 65.6 |

Comparative Example 1

The adsorption desulfurization was conducted in the same manner as Example 1, except that the airflow particle sorter was replaced with a stainless steel filtering tube filter (which was the same as that in the catalyst fine powder catcher of Example 1, but the cylindrical shell was not used, and the number of the stainless steel filtering tube filter was only one). After the reaction, the hydrocarbon mixture was sent from the filter outlet to the subsequent refining and processing unit.

The reaction was continuously conducted for 500 hours. During the reaction, the composition of the obtained hydrocarbon product, and the average particle size of the catalyst in the catalyst dense bed of the fluidized bed reactor were monitored. The results were listed in Table 5. After 500 hours of reaction, in the catalyst in the dense bed of the fluidized bed reactor, the content of the catalyst having a particle size of less than 30 μm was 26.5 wt %. A total of 14.2 kg catalyst was charged into the fluidized bed reactor before the reaction, and a total of 0.3 kg catalyst was supplemented to the fluidized bed reactor during the reaction.

TABLE 5

| | Time/h | | | | |
|---|---|---|---|---|---|
| | 100 | 200 | 300 | 400 | 500 |
| Sulfur content of the product/wppm | 4.5 | 8.2 | 11.8 | 14.6 | 32.4 |
| Filter blowback interval/second | 300 | 210 | 150 | 100 | 65 |
| Antiknock index reduction value | 0.52 | 0.58 | 0.66 | 0.55 | 0.72 |
| Average particle size in the dense bed/μm | 65.3 | 58.7 | 54.3 | 48.5 | 47.6 |

Comparative Example 2

The adsorption desulfurization was conducted in the same manner as Example 1, except that the airflow particle sorter was replaced with a cyclone separator, wherein the intake port of the cyclone separator (the number of the intake port was one) had a diameter of 30 mm, the intake port was installed in the upper part of the straight tube zone in the tangential direction, wherein the upper edge of the intake port was aligned with the top of the straight tube zone, the diameter of the straight tube zone was 40 mm, the height of the straight tube zone was 48 mm, the height of the cone zone was 68 mm, the linear velocity of the hydrocarbon-catalyst mixture coming from the settling zone at the intake port was 18 m/s, and the linear velocity of the hydrocarbon-catalyst mixture in the cyclone separator at the outtake port was 20 m/s.

The reaction was continuously conducted for 500 hours. During the reaction, the composition of the obtained hydrocarbon product, the average particle size of the catalyst in the catalyst fine powder storage tank, and the average particle size of the catalyst in the catalyst dense bed of the fluidized bed reactor were monitored. The results were listed in Table 6. After 500 hours of reaction, in the catalyst in the dense bed of the fluidized bed reactor, the content of the catalyst having a particle size of less than 30 μm was 22.3 wt %. A total of 14.2 kg catalyst was charged into the fluidized bed reactor before the reaction, a total of 1.7 kg catalyst was supplemented to the fluidized bed reactor during the reaction; and 2.3 kg fine catalyst powder was collected in the catalyst fine powder storage tank after 500 hours.

TABLE 6

| | Time/h | | | | |
|---|---|---|---|---|---|
| | 100 | 200 | 300 | 400 | 500 |
| Sulfur content of the product/wppm | 4.5 | 8.2 | 11.8 | 14.6 | 32.4 |
| Antiknock index reduction value | 0.52 | 0.58 | 0.66 | 0.55 | 0.72 |

TABLE 6-continued

|  |  | Time/h | | | | |
| --- | --- | --- | --- | --- | --- | --- |
|  |  | 100 | 200 | 300 | 400 | 500 |
| Average particle size of the catalyst/μm | Fine powder storage tank | 8.2 | 8.5 | 8.9 | 9.5 | 9.4 |
|  | Catalyst dense bed | 67.2 | 57.8 | 56.3 | 48.9 | 48.5 |

It could be seen by comparing Example 1 and Comparative Example 1 that the adsorption desulfurization of the sulfur-containing hydrocarbon feedstock with the adsorption desulfurization reaction apparatus of the present invention not only could effectively and stably remove the sulfur element in the hydrocarbon feedstock, but also could duly send the fine catalyst powder produced in the system out of the fluidized bed reactor. During the separation of the hydrocarbon-catalyst mixture, no or substantially no secondary crushing of catalyst particles appeared, therefore the accumulation of fine catalyst powder in the fluidized bed reactor could be effectively prevented, and the long and stable operation of the adsorption desulfurization reaction apparatus could be assured.

It could be seen by comparing Example 1 and Comparative Example 2 that upon using the cyclone separator as the internal separator of the fluidized bed reactor, the catalyst consumption would remarkably increase, and the particle size of the fine catalyst powder in the catalyst fine powder storage tank became smaller. This demonstrated that upon using the cyclone separator to separate and sort the hydrocarbon-catalyst mixture, there was a high probability for secondarily crushing catalyst particles. Upon using the cyclone separator to conduct the separation and sorting, due to the high content of the fine catalyst powder in the fluidized bed reactor, the desulfurization efficiency was therefore reduced and it was difficult to obtain a satisfactory desulfurization effect.

Example 3

The adsorption desulfurization was conducted in the same manner as Example 1, except that the straight tube zone of the airflow particle sorter was installed with 6 directing-intake ports in its tangential direction (the directing-intake ports were distributed in the circumferential direction of the straight tube zone (as shown in FIG. 2), and each of the directing-intake ports had the same cross-section area perpendicular to the airflow direction); the outtake tube of the airflow particle sorter was installed with 6 directing-outtake ports in its tangential direction (the directing-outtake ports were distributed in the circumferential direction of the outtake tube (as shown in FIG. 2), and each of the directing-outtake ports had the same cross-section area perpendicular to the airflow direction);

the difference between the horizontal cross-section area of the straight tube zone and the horizontal cross-section area of the outtake tube was A0, the total cross-section area perpendicular to the airflow direction of the directing-intake port was A1, the total cross-section area perpendicular to the airflow direction of the directing-outtake port was A2, A1/A0 was 0.4:1, A2/A0 was 0.25:1; the ratio of the cross-section area perpendicular to the airflow direction of the outtake tube to the horizontal cross-section area of the straight tube zone was 0.167:1; the distance from the lower edge of the directing-intake port to the bottom of the straight tube zone was H1, the distance from the lower edge of the directing-outtake port to the bottom of the straight tube zone was H2, the ratio of H1/H2 was 1:0.4; the ratio of the total cross-section area perpendicular to the airflow direction of the directing-intake port to the horizontal cross-section area of the settling zone was 0.09:1.

The temperature for contacting the sulfur-containing hydrocarbon feedstock and hydrogen gas with the adsorption desulfurization catalyst was 410° C., the pressure by gauge was 30 atm, and the weight hourly space velocity of the sulfur-containing hydrocarbon feedstock was 4 $h^{-1}$.

The linear velocity of the hydrocarbon-catalyst mixture at the directing-intake port of the airflow particle sorter was 5 m/s, and the linear velocity at the directing-outtake port of the airflow particle sorter was 8 m/s.

The reaction was continuously conducted for 500 hours. During the reaction, the composition of the obtained hydrocarbon product, the average particle size of the catalyst in the catalyst fine powder storage tank, and the average particle size of the catalyst in the catalyst dense bed of the fluidized bed reactor were monitored. The results were listed in Table 7. After 500 hours of reaction, in the catalyst in the dense bed of the fluidized bed reactor, the content of the catalyst having a particle size of less than 30 μm was 10.8 wt %. A total of 14.2 kg catalyst was charged into the fluidized bed reactor before the reaction, a total of 1.44 kg catalyst was supplemented to the fluidized bed reactor during the reaction; and 1.95 kg fine catalyst powder was collected in the catalyst fine powder storage tank after 500 hours.

TABLE 7

|  |  | Time/h | | | | |
| --- | --- | --- | --- | --- | --- | --- |
|  |  | 100 | 200 | 300 | 400 | 500 |
| Sulfur content of the product/wppm |  | 4.2 | 3.8 | 3.7 | 3.5 | 4.1 |
| Antiknock index reduction value |  | 0.65 | 0.57 | 0.63 | 0.53 | 0.48 |
| Average particle size of the catalyst/μm | Fine powder storage tank | 14.2 | 16.7 | 17.2 | 17.8 | 18.5 |
|  | Catalyst dense bed | 72.5 | 68.9 | 67.8 | 66.9 | 66.3 |

Example 4

The adsorption desulfurization was conducted in the same manner as Example 3, except that $A_1/A_0$ was 0.25:1, $A_2/A_0$ was 0.167:1, the linear velocity of the hydrocarbon-catalyst mixture at the directing-intake port of the airflow particle sorter was 5 m/s, and the linear velocity at the directing-outtake port of the airflow particle sorter was 10 m/s.

The reaction was continuously conducted for 500 hours. During the reaction, the composition of the obtained hydrocarbon product, the average particle size of the catalyst in the catalyst fine powder storage tank, and the average particle size of the catalyst in the catalyst dense bed of the fluidized bed reactor were monitored. The results were listed in Table 5. After 500 hours of reaction, in the catalyst in the dense bed of the fluidized bed reactor, the content of the catalyst having a particle size of less than 30 μm was 11.3 wt %. A total of 14.2 kg catalyst was charged into the fluidized bed reactor before the reaction, a total of 1.46 kg catalyst was supplemented to the fluidized bed reactor during the reaction; and 1.99 kg fine catalyst powder was collected in the catalyst fine powder storage tank after 500 hours.

TABLE 8

|  |  | Time/h | | | | |
| --- | --- | --- | --- | --- | --- | --- |
|  |  | 100 | 200 | 300 | 400 | 500 |
| Sulfur content of the product/wppm | | 3.5 | 3.9 | 4.5 | 4.2 | 3.7 |
| Antiknock index reduction value | | 0.58 | 0.61 | 0.56 | 0.45 | 0.60 |
| Average particle size of the catalyst/μm | Fine powder storage tank | 13.5 | 14.7 | 16.3 | 17.9 | 18.8 |
| | Catalyst dense bed | 71.3 | 70.8 | 68.7 | 68.0 | 67.8 |

The invention claimed is:

1. An adsorption desulfurization reaction apparatus, comprising:
a fluidized bed reactor, a catalyst regenerator, a catalyst reducer, a catalyst fine powder catcher, and a fine powder classificator,
the fluidized bed comprises a top-sealed reactor main body, at least one airflow particle sorter, and at least one stream inlet, wherein the reactor main body comprises a settling zone and a reaction zone, wherein the settling zone is disposed above the reaction zone and the at least one stream inlet is located at the bottom of the reaction zone,
wherein the at least one airflow particle sorter comprises a top-sealed sorter main body, a discharge port, an outtake tube, and at least one directing-intake port,
wherein the sorter main body comprises a straight tube zone and a cone zone, wherein the straight tube zone is disposed above the cone zone and is connected to a conical bottom of the cone zone, and the discharge port is located at the bottom of the cone zone,
wherein the at least one directing-intake port is installed in an upper part of the straight tube zone in a tangential direction of the straight tube zone, and is in communication with an inner space of the sorter main body,
wherein the outtake tube is hermetically inserted into the top of the sorter main body and extends downwardly to a lower part of the straight tube zone, and the outtake tube has a sealed bottom end,
wherein the lower part of the outtake tube is provided with at least one directing-outtake port installed in a tangential direction of the outtake tube, connecting the outtake tube with the inner space of the sorter main body,
wherein the sorter main body is located in the settling zone, the at least one directing-intake port is communicated with the settling zone, and the discharge port downward extends into the reaction zone, and the outtake tube hermetically passes through the fluidized bed reactor,
wherein the catalyst fine powder catcher is provided outside of the reactor main body, the catalyst fine powder catcher comprises a feed port that communicates with the outtake tube of the at least one airflow particle sorter, and a discharge tube in communication with a feed port of the fine powder classificator,
wherein the fine powder classificator comprises a discharge tube for receipt of catalyst particles sorted out by the fine powder classificator, hermetically passing through a side wall of the reactor main body and extending into the reaction zone.

2. The adsorption desulfurization reaction apparatus of claim 1, wherein, in the fluidized bed reactor, a ratio between a total cross-section area perpendicular to the airflow direction of the at least one directing-intake port of the at least one airflow particle sorter to a horizontal cross-section area of the settling zone is 0.01-0.4:1.

3. The adsorption desulfurization reaction apparatus of claim 2, wherein said ratio is 0.05-0.3:1.

4. The adsorption desulfurization reaction apparatus of claim 1, wherein, in the at least one airflow particle sorter, a ratio between a length of the outtake tube inside the sorter main body to a length of the straight tube zone is in a range of 0.6-1:1, 0.7-1:1, 0.8-1:1, 0.9-1:1, or 0.95-1:1.

5. The adsorption desulfurization reaction apparatus of claim 1, wherein, in the at least one airflow particle sorter, the cone zone is in a shape of an inverse truncated cone.

6. The adsorption desulfurization reaction apparatus of claim 1, wherein, in the at least one airflow particle sorter, a ratio between a height of the straight tube zone to a height of the cone zone is in a range of 0.4-1.5:1, 0.5-1:1, or 0.6-0.8:1.

7. The adsorption desulfurization reaction apparatus of claim 1, wherein, in the at least one airflow particle sorter, a number of the at least one directing-intake port and a number of the at least one directing-outtake port are identical.

8. The adsorption desulfurization reaction apparatus of claim 1, wherein, in the at least one airflow particle sorter, when a distance from a lower edge of the at least one directing-intake port to a bottom of the straight tube zone is H1 and a distance from the lower edge of the at least one directing-outtake port to a bottom of the straight tube zone is H2, then a ratio of H1/H2 is in a range of 1:0.1-0.8 or 1:0.2-0.6.

9. The adsorption desulfurization reaction apparatus of claim 1, wherein, in the at least one airflow particle sorter, an upper edge of the at least one directing-intake port is aligned with a top of the straight tube zone.

10. The adsorption desulfurization reaction apparatus of claim 1, wherein, in the at least one airflow particle sorter, a lower edge of the at least one directing-outtake port is aligned with a bottom of the outtake tube.

11. The adsorption desulfurization reaction apparatus of claim 1, wherein, in the at least one airflow particle sorter, when a difference between a horizontal cross-section area of the straight tube zone and a horizontal cross-section area of the outtake tube is A0, a total cross-section area perpendicular to the airflow direction of the at least one directing-intake port is A1, and the total cross-section area perpendicular to the airflow direction of the at least one directing-outtake port is A2, then A1/A0 is in a range of 0.01-0.8:1 or 0.02-0.6:1, and A2/A0 is in a range of 0.01-0.5:1 or 0.015-0.4:1.

12. The adsorption desulfurization reaction apparatus of claim 1, wherein, in the at least one airflow particle sorter, a ratio between the cross-section area perpendicular to the airflow direction of the outtake tube to a horizontal cross-section area of the straight tube zone is in a range of 0.01-0.7:1 or 0.04-0.6:1.

13. The adsorption desulfurization reaction apparatus of claim 1, wherein the at least one airflow particle sorter has more than one directing-intake ports distributed circumferentially about the straight tube zone.

14. The adsorption desulfurization reaction apparatus of claim 1, wherein the at least one airflow particle sorter comprises more than one directing-outtake ports distributed circumferentially about the outtake tube.

15. An adsorption desulfurization process comprising:
providing an adsorption desulfurization reactor apparatus of claim 1;
contacting a sulfur-containing hydrocarbon feedstock and an adsorption desulfurization catalyst in the reaction zone of the fluidized bed reactor to form a hydrocarbon-catalyst mixture, wherein at least a portion of sulfur element in the hydrocarbon feedstock is adsorbed by the adsorption desulfurization catalyst; and
subjecting the hydrocarbon-catalyst mixture successively to separation in the settling zone, the at least one airflow particle sorter, the catalyst fine powder catcher, and the fine powder classificator to obtain a hydrocarbon product stream and a spent catalyst.

16. The adsorption desulfurization process of claim 15, wherein the reaction zone has an atmosphere that contains hydrogen gas.

17. The adsorption desulfurization process of claim 16, wherein a molar ratio of the hydrogen gas to the sulfur-containing hydrocarbon feedstock is in range of 0.1-2:1, 0.15-1.5:1, or 0.2-1:1.

18. The adsorption desulfurization process of claim 15, wherein reaction conditions inside the fluidized bed include a temperature of 300-500° C., a gauge pressure of 5-50 atm, a weight hourly space velocity of the sulfur-containing hydrocarbon feedstock of 1-15 $h^{-1}$, and a density of a catalyst dense bed of 100-700 $kg/m^3$.

19. The adsorption desulfurization process of claim 15, wherein a ratio between an inlet linear velocity of the hydrocarbon-catalyst mixture from the settling zone at the at least one directing-intake port of the at least one airflow particle sorter to an inlet linear velocity of the hydrocarbon-catalyst mixture in the sorter main body at the at least one directing-outtake port is in a range of 1:1.2-2.5 or 1:1.5-2.

20. The adsorption desulfurization process of claim 15, wherein an inlet linear velocity of the hydrocarbon-catalyst mixture from the settling zone at the at least one directing-intake port of the at least one airflow particle sorter is in a range of 0.8-10 m/s, 1-8 m/s, or 1.5-5 m/s; and an inlet linear velocity of the hydrocarbon-catalyst mixture in the sorter main body of the at least one airflow particle sorter at the at least one directing-outtake port is 1.5-16 m/s, 2-12 m/s, or 2.5-10 m/s.

* * * * *